United States Patent [19]

Thomas

[11] Patent Number: 4,459,288

[45] Date of Patent: Jul. 10, 1984

[54] THERAPEUTIC BLOOD CLOTTING FACTOR COMPOSITIONS AND THEIR USE

[75] Inventor: William R. Thomas, Laguna Niguel, Calif.

[73] Assignee: Baxter Travenol Laboratories, Inc., Deerfield, Ill.

[21] Appl. No.: 360,305

[22] Filed: Mar. 22, 1982

Related U.S. Application Data

[62] Division of Ser. No. 262,286, May 11, 1981, Pat. No. 4,357,321, which is a division of Ser. No. 116,186, Jan. 28, 1980, Pat. No. 4,287,180.

[51] Int. Cl.$^3$ .............................................. A61K 35/14
[52] U.S. Cl. .................................................... 424/101
[58] Field of Search ......................................... 424/101

[56] References Cited

U.S. PATENT DOCUMENTS 3,717,708  2/1973  Wada et al. .......................... 424/177
4,067,964  1/1978  Schwinn et al. ..................... 424/105
4,170,590  10/1979  Stephan et al. ................. 260/112 B

FOREIGN PATENT DOCUMENTS 14333  8/1980  European Pat. Off. .
80/00069  11/1980  European Pat. Off. .

OTHER PUBLICATIONS

Kotitschke et al., Deutsche Arbeitsgemeinschaft fuer Blutgerinnungsforschung, Immunologische Probleme de Blutgerinnung von Willebrand-Jurgens Syndrom: Verhandlungsbericht der Deutschen . . . Feb. 19–21, 1976 NY: Schattauer, 1978, pp. 317–324.
Steinbuch et al., "Chemical Abstracts" 66:9221p (1967).
Lanchantin et al., "Chemical Abstracts" 60:8268d (1964).
Elodi et al., "Chemical Abstracts" 89:104753b (1978).
Heystek et al., "Biological Abstracts" 60:41424 (1975).
Soulier, "Proceedings of the 8th Congress of European Society of Hematology" Article 388, Vienna (1961).
Schiff, "Chemical Abstracts" 72:98135g (1970).
Bruning et al., "Chemical Abstracts" 75:149582x (1971).
Eggeling et al., "Chemical Abstracts" 84:174032m (1976).
Kotitschke et al., "Chemical Abstracts" 91:9396v (1979).
Suomela et al., Chem. Abst., vol. 87 (1977), p. 51425w.
Yoshioka, Chem. Abst., vol. 89 (1978), p. 213,384c.
Yue et al., Chem. Abst., vol. 86 (1977), p. 116,298h.

Primary Examiner—Sam Rosen
Attorney, Agent, or Firm—Marjorie D. Hunter; Paul C. Flattery

[57] ABSTRACT

Compositions including, in units/ml, factor VIII correctional activity, about from 2–35; prothrombin, about from 1–10; thrombin, less than about 0.003; factor VII, about from 37–190; factor VIIa, about from 8–80; total factor IX, about from 15–112; factor IX precursor, 0 to about 30; factor X, about from 1–30; and factor Xa, about from 1–10 are used in therapeutically effective amounts to treat blood clotting factor inhibitors.

18 Claims, No Drawings

THERAPEUTIC BLOOD CLOTTING FACTOR COMPOSITIONS AND THEIR USE

This is a division of application Ser. No. 262,286, filed May 11, 1981, now U.S. Pat. No. 4,357,321 which in turn is a division of Ser. No. 116,186, filed Jan. 28, 1980 and now U.S. Pat. No. 4,287,180.

BACKGROUND OF THE INVENTION

This invention relates to the treatment of blood coagulation pathologies. The invention generally deals with novel methods for preparing new compositions useful in the management of hemorrhagic episodes in patients with inhibitors of blood clotting factors. In particular, the invention is concerned with the therapy of antihemophilic factor or plasma thromboplastin component inhibitors.*

*The term inhibitor in this patent refers to a specific antibody to either antihemophilic factor in Hemophilia A patients or to plasma thromboplastin component in Hemophilia B patients.

Blood coagulation is an exceedingly complex process. The interaction of various blood components which eventually gives rise to a fibrin clot has been compared to a cascade of steps, each of which is dependent upon and regulated by preceding and following steps. Generally, the blood components which take part in the coagulation cascade are either proenzymes or enzyme modulators. The proenzymes are enzymatically inactive proteins which are converted to proteolytic enzymes by the action of an "activator", generally another proteolytic enzyme produced at an earlier stage in the coagulation cascade. Coagulation factors which have undergone such a conversion are hereafter defined as activated factors, and designated by the lower case postscript "a" while the proenzymes are referred to as precursor clotting factors.

The enzyme modulators are principally cofactors such as calcium ions or nonenzyme proteins and most are essential if the enzymes are to exhibit any catalytic activity at all. Such modulators are to be distinguished from enzyme substrates. Substrates are compounds which are covalently modified by an enzyme while modulators or cofactors merely bind to the enzyme without undergoing a change in structure.

Blood coagulation is best visualized as a cascade of reactions between formed and soluble blood components in which most segments of the cascade are demarked by a proenzyme. An initial event such as the contact activation of Hageman factor (factor XII) will start one branch of the cascade. Basically, the product of this initial event then activates the next proenzyme in the cascade and so on in a sequential process until a fibrin clot is formed, the total rate of the cascade being dependent upon cofactors and modulators.

While much is now known about the various blood coagulation factors and the manner in which they interact and are susceptible to environmental influences, there remain many areas where questions remain. One such area is the action, etiology and therapeutic treatment of blood clotting factor inhibitors.

Inhibitors of blood clotting factors pose substantial difficulties in conventional hemorrhage therapy. Uncontrolled bleeding due to coagulation deficiencies is usually halted by supplying the deficient component from pooled plasma sources. However, since inhibitors are frequently elucidated by the patient in response to the presence of the deficient clotting factor, this conventional approach is frequently counterproductive since increasing the dosage of clotting factor merely results in greater output of inhibitor. This problem with clotting factor inhibitors is not an isolated one. For example, up to an estimated 21% of the Hemophilia A population develops factor VIII inhibitor, i.e., antihemophilic factor (AHF) inhibitor. To fully understand the background of this invention it is necessary to discuss the mechanisms of blood clotting and the influence of inhibitors thereon.

The etiology of such clotting factor inhibitors is not well defined, but is thought to be along two principal routes. First, as explored above, frequent infusions of therapeutic clotting factor concentrates such as AHF frequently produce an immune response in patients as evidenced by increased inhibitor titer. Multiple challenges of the patient's immune system with AHF are believed to stimulate ever-increasing AHF antibody levels. Since such antibodies may then complex with the AHF and block its activity, the increases in antibody titer dictate greater doses to achieve a satisfactory clinical response.

In contrast, the second route of appearance for the inhibitors is not believed to be a function of the administration of therapeutic blood protein fractions. Rather, the inhibitor seemingly arises spontaneously in the manner of an idiopathic or autoimmune disease, frequently following on the heels of drug reactions or collagen disorders.

The medical community has dealt with clotting factor inhibitors by (a) administering either extremely low or extremely high doses of the clotting factor which is being inhibited, with or without immunosuppression, (b) using clotting factor of non-human origin or (c) administering activated prothrombin complex concentrates (PCC), i.e., PCC in which at least a small proportion of the clotting factors have been converted to active enzymes. The first two techniques have not been widely used. The infusion of sufficiently large amounts of clotting factor to overwhelm the inhibitor existing in the patient's system becomes less and less effective with each treatment episode because inhibitor titers rise in response to each administration of clotting factor. On the other hand using non-human clotting factor creates a risk of severe immune reactions in treated patients.

The use of activated PCC for the treatment of patients afflicted with clotting factor inhibitors has received widespread acceptance, following a presentation by Fekete et al. at the XIV International Congress of Hematology in 1972. For example, see Kurczynski et al., "New England Journal of Medicine" 291(4):164 (1974) wherein an activated PCC containing 15 units of factor II/ml (the term "factor" will be frequently abbreviated herein as "F"), 200 units of F-VII/ml, 42 units of F-IX/ml, 58 units of F-X/ml, 3–10 units of F-IXa/ml, 3–8 units of F-Xa/ml and 0.001–0.003 units of thrombin/ml was used therapeutically to treat F-VIII inhibitor afflicted patients. The clinical success of such concentrates has been ascribed to the presence of the various activated cotting factors VIIa, IXa of Xa, or thrombin, although the identity of the operative activated factor or factors is subject to controversy. Recently, success has also been attributed to the presence of a component possessing "factor eight inhibitor bypassing activity" (FEIBA). This component is not believed to be one of the activated factors II, VII, IX or X, but otherwise the nature of its activity is not well defined.

Activated PCC, when used to treat factor-VIII inhibitor, has the advantage that the complex can be tailored to be sufficiently free of factor VIII antigen that an immune response in humans are not observed.

The activated factors which are present in most of the prothrombin complex concentrates previously used to treat clotting factor inhibitors are artifacts of the plasma fractionation procedure in which prothrombin complex is enriched from Cohn fraction I supernatant; the activated factors were not induced by any special steps and as a result were often considered to be in too low or too variable a concentration to be satisfactory.

While processes for the activation of PCC have been generally alluded to in the art, the only detailed disclosure known to applicants of a protocol for manufacturing such products appears in U.S. Pat. No. 4,160,025, to Eibl et al. These patentees urge that before their method was developed, activated prothrombin complex concentrates "could not be tested as regards their effective principle and could not be standardized . . . therefore the results [were] not safe and [could] hardly be repeated." The patentees go on to state that their method "has as its object to safeguard in a repeatable and deliberate manner a generation of the desired factor-VIII-inhibitor-bypassing activity" (two paragraphs bridging columns 1 and 2).

The Eibl et al. method comprises activating a starting material selected from plasma, cryoprecipitate-poor plasma or Cohn fraction I supernatant by use of a contact activator, followed by adsorption of the FEIBA component and factors II, VII, IX and X onto a basic ion exchanger. Contact activators are well known substances such as silica or kaolin which initiate the intrinsic coagulation mechanism by activation of Hageman factor.

While Eibl et al. are highly concerned with standardizing their final product they give scant attention to the activation procedure. The pH, temperature, starting materials and activators are generally described but no mention is made of the activation period other than the one or three hours disclosed in Examples 1 and 2.

It is extremely difficult to avoid excessive activation of prothrombin complex concentrates because the activation reactions, being an enzyme cascade, tend to accelerate rapidly at variable and largely unpredictable rates which are controlled by substances in the activated sample and by the kinetics of the enzymes in question. The most potentially harmful result of excessive activation is the appearance of thrombin, or activated factor II in the product. For example, Eibl et al. report thrombin levels of 0.05 and 0.07 NIH units/ml. Thrombin is not considered desirable because it is capable of acting directly on blood components to yield a fibrin clot while other activated clotting factors exert their effect earlier in the coagulation cascade and hence are more likely to be subject to modulation by blood components in vivo. The elevated thrombin levels reported by Eibl et al. are believed by applicant to be a function of the failure of Eibl et al. to adequately control the activation procedure. Eibl et al. do not screen the starting material for activation, thus failing to taken into account the pre-existing activation state of each lot of plasma or plasma fraction used, and do not determine the in-process response of the lot to activation. However, Eibl et al. do suggest in Example 1 that variations in the clotting factor and FEIBA levels in various lots of final product may be compensated for by mixing bulk batches until the desired ratio of clotting factors to FEIBA is achieved. This is unsatisfactory because of costs, yield losses and contamination risk inherent in such a procedure. Further, thrombin is frequently undesirably elevated, even in products which were apparently manufactured by following this procedure.

According to White et al., "Blood" 49 (2): 159–170 (1977), American Red Cross PCC is nonthrombogenic in part because of the presence of heparin and the deliberate fortification with antithrombin III. These two additives are said to result in the irreversible inactivation of proteases in PCC. White et al. did not report treating inhibitor patients with such PCC; it is problematic that such a concentrate would be useful for this purpose where any activated factors which might inadvertently be present, as well as mechanisms for their generation, are suppressed by heparin and antithrombin III.

It is accordingly an object of this invention to standardize activated PCC preparations without mixing or handling the finished product.

It is an additional object to control the manufacture of activated PCC to reduce the production of thrombin during the process and to neutralize any thrombin which is produced.

It is another object to treat patients having clotting factor inhibitors or deficiencies with an activated PCC containing selected activities of factors II, VII, total IX, X, VIIa, IX precursor, and Xa.

These and other objects of the invention will be apparent to those skilled in the art from consideration of the specification taken as a whole.

The principal object of this invention is accomplished by determining in advance of the completion of activation the conditions needed to achieve an activated PCC of substantially predetermined composition. This is in contrast to the passive approach to the unsolved problems of standardization and thrombogenicity which characterizes the published prior art, where conditions such as the time and temperature of activation are arbitrarily set and any difficulty with the resulting product is remedied, if possible, by selecting lots which when combined will yield the desired products. Accordingly, in a method wherein a prothrombin ciomplex-containing blood protein fraction is activated under conditions which produce enzymatically active blood clotting factors, the improvement comprises (a) selecting at least one of said conditions which is to be varied to control the degree of activation;
(b) prior to the completion of activation, determining the magnitude of the condition needed to activate the fraction to a predetermined degree of activation;
(c) setting the condition to said magnitude; and
(d) conducting the activation of the fraction in accordance with said condition.

Generally only one condition of the activation is permitted to vary, and this is usually the period of time that activation is allowed to proceed.

The magnitude of the selected condition is determined in one of two ways, or a combination of both. In the least preferred of the two methods, the condition is determined by removing aliquots of the fraction after activation has been commenced, terminating the activation of each aliquot, determining the degree of activation of each aliquot and calculating the magnitude of the condition necessary to achieve a predetermined degree of activation of the fraction.

Alternatively, the condition magnitude may be determined by removing aliquots of the fraction prior to activation, varying the condition among the aliquots, activating the aliquots in accordance with the condition set for each aliquot, terminating the activation, determining the degree of activation of each aliquot and calculating the magnitude of the condition necessary to achieve a predetermined degree of activation of the fraction. This embodiment has the advantage than one cannot overrun the predetermined activation level, as could be done during the assay of aliquots withdrawn from a bulk lot which is simultaneously undergoing activation.

Control of the activation process is also facilitated by selecting as starting materials only fractions which exhibit a low degree of spontaneous activation.

The degree of activation is generally monitored by following the nonactivated partial thromboplastin (NAPT) or factor VIII correctional times although thrombin determinations are also useful. These assays are fully described below. The levels of individual clotting factors, may also be determined as a measure of activation. Methods for determining these factors are also described therein.

An additional object of this invention is accomplished by activating an intermediate PCC produced during the method of U.S. Pat. No. 3,560,475. Selection of a particular point in the patented method to activate the PCC greatly facilitates the control of the activation procedure because of the presence in the PCC of an activation retardant.

A further object is achieved by adding heparin to the activated product after the activation retardant has been neutralized or removed, generally immediately before the product is filled into containers and lyophilized.

A further object is accomplished by including the stabilizers heparin and, optionally, antithrombin III in the final activated PCC. These substances inactivate thrombin and are believed to provide a margin of safety against thrombosis in susceptible patients, e.g., those with liver dysfunction.

This invention also includes an improved activated PCC composition which comprises an aqueous solution having clotting factor activities, in units/ml, of F-II, 1–10; thrombin, less than about 0.003; F-VII, about from 37 to 190; F-VIIa, about from 8 to 80; total F-IX, about from 15 to 112; F-IX precursor, 0 to about 30; F-X, about from 1 to 30; and F-Xa, about from 1 to 10. More particularly, the improved activated PCC will contain certain delineated levels of total F-IX and F-IX precursor, F-VII and F-VIIa, F-X and F-Xa, F-VIII correctional activity and NAPT time, and will be sufficiently free of factor VIII antigen to not produce an immune response in patients to whom the activated PCC is administered.

DESCRIPTION OF THE PREFERRED EMBODIMENTS

Suitable starting materials for use herein should at least contain clotting factors II, VII, IX, X, XI and XII. The starting compositions will generally be solutions of Cohn plasma fractions I+II+III, I and III, II and III, III, III-0, IV-1 and IV-4; IV-1 is preferred. The compositions should be dissolved in buffer or saline to a concentration of about 10% weight/volume at about 20° C. and then screened for clotting factor activity as described below to determine the degree of pre-existing spontaneous activation. The coagulation factors are then partially purified by adsorption onto a suitable known prothrombin complex adsorbent, e.g., tribasic calcium phosphate, as described in U.S. Pat. No. 3,560,475, or a diethylamino ethyl group substituted resin, followed by elution from the adsorbent in a volume of eluting solvent equal to about 4% of the volume of the dissolved Cohn fraction. None of these volumes or temperatures are critical.

The starting materials are then preferably assayed to detect any which might have inadvertently been spontaneously activated to a high degree. Whether or not a starting composition is suitable is determined by assaying the NAPT time and, preferably, the factor VIII correctional time of the fraction. The former is a conventional assay, disclosed for example by Pepper et al., "British Journal of Haematology" 36:573 (1977) or Kingdon et al., Abstract #86 of the meeting of the American Society of Hematology, Atlanta (1974). It is preferred that the starting material be diluted within the range of 1:10 to 1:1000 in Tris buffered saline, optimally 1:100, before determination. If the sample is used at full strength the clotting time is often excessively rapid. Since the NAPT time has as its readout signal the formation of a plasma clot, the test results are usually reported in seconds when a 1:100 dilution is used. All references to the NAPT time herein are for assays on 1:100 dilutions of the sample or standard in a solution of 0.06 M Tris in saline at pH 8.3 (hereinafter Tris buffered saline).

The factor VIII correctional assay comprises the following steps, all conducted at 37° C. Aliquots of the composition to be tested are diluted in a barbital buffer to give dilutions of 1:20, 1:40, and 1:80. This barbital buffer is a modification of the diluting fluid (described in Proctor, et al., Am.J.Clin.Path. 36(3):214 (1961) which is made by mixing one part of diluting fluid with one part of water. 1:20, 1:40 and 1:80 dilutions of reference activated PCC having one unit of F-VIII correctional activity/ml are made into the diluting fluid as with the unknowns. For the purposes herein, 1 unit of factor VIII correctional activity is defined as that quantity of a 1:20 dilution into diluting fluid of activated PCC which, upon addition to factor VIII deficient or inhibitor plasma having less than 5% of the factor VIII activity of normal human plasma, will correct the clotting time of that plasma to 35 seconds under the conditions of the above assay. Reagent blanks are prepared in the same fashion as the standards.

In the conduct of the assay, 0.1 ml of a mixture of soluble ellagic acid (available commercially from Dade under the trademark Actin) is added to a set of prewarmed fibrometer reaction cups. 0.1 ml of factor VIII deficient plasma having less than 5% of the factor VIII activity of normal pooled human plasma is then added to each cup. 0.1 ml each of aliquot, blank or standard dilution is added immediately to a cup containing the mixture of ellagic acid and factor VIII deficient plasma. After three minutes 0.1 ml of 0.02 M $CaCl_2$ is added to each cup to initiate clotting. The clotting time is recorded and corrected for the reagent blank clotting, if necessary.

The factor VIII correctional activity in units is calculated by averaging the replicates and plotting the reference concentrations, as established by the dilutions, against the respective clotting times. The concentration of each diluted sample can be located from the plot, corrected for its dilution and the average concentrations reported in units/ml. It is preferred to simply report the factor VIII correctional assay results in seconds where screening the starting materials or determining activation conditions. However, the potency of the final product is generally reported in units/ml. When screening the starting fractions, dilutions are made in a non-modified diluting fluid.

Starting materials having a NAPT time of greater than about 200 seconds and a factor VIII correctional time of more than about 89 seconds are acceptable for use in the process of this invention. For example, in a group of 30 Cohn fraction IV-1 pastes, each of which was prepared from a different plasma pool, the NAPT time ranged from 144 to 294 seconds and the factor VIII correctional time from 82.7 to 98 seconds. It is preferred to screen the starting materials for thrombin as well, and, in such cases, starting material should not be used if it contains sufficient thrombin to form a clot within 2 hours in the assay described below, i.e., less than about 0.001 units/ml of thrombin. Also, the starting materials should contain about from 0.4 to 1.0 units/ml of prothrombin, about from 0.5 to 3.0 units of F-VII/ml, 0.5-1.5 units of F-IX/ml and 0.5-3.0 units of F-X/ml.

The effectiveness of feedback assays to establish the extent of activation can be improved by slowing the rate of activation sufficiently to allow a generous period in which to conduct the assays. This reduces the chance of exceeding the predetermined activation state while performing the assays. One convenient technique for slowing the activation rate is to activate the coagulation factors in the presence of a plasma component which will be referred to hereinafter as an activation retardant. The activation retardant slows the rate of activation and is defined as a substance which is removed or neutralized during the process of adsorbing a 10% solution of Cohn fraction IV-1 paste onto 0.5% by weight of tribasic calcium phosphate at pH 7.2, eluting from the calcium phosphate with 0.1M sodium citrate and precipitating from the calcium phosphate eluate at a PEG concentration of 5%. The identity of retardant is unknown, but has been hypothesized to be antithrombin III or unidentified diluent proteins which slow the rate of activation. The amount of antithrombin III remaining in the calcium phosphate eluate is about 1 International Unit/ml, while the product after PEG precipitation contains about 0.1 Unit/ml.

Once a suitable starting material preferably containing the activation retardant has been selected, a procedure is instituted to convert at least inactive proenzyme to the corresponding active blood clotting factor, hereinafter the activation procedure. This is conventionally done by contact activating plasma or plasma fractions. This is accomplished by mixing a contact activator such as kaolin, silica or silicates with the starting material and continuing to mix until the desired activation state is achieved. Contact activators are well known and the selection of any one is not critical. However, it is preferable to use an insoluble activator so as to facilitate its removal when the desired degree of activation is accomplished. Silica is preferred. The contact activator is used in a concentration of about from 0.05 to 5% weight by volume preferably about 0.06%. The average temperature of activation may range from 0° C. to about 30° C., and preferably is about 15° C. The pH may range about from 5.5 to 8.5, but is preferably about 7.2. The protein concentration ranges about from 0.3 to 0.9 gm%.

The extent of activation is usually controlled by holding all of these conditions constant but one, and varying that one to yield the predetermined degree of activation. It is preferred to control the activation period by holding pH, temperature and other conditions constant while varying the reaction time. This is convenient because the reaction is readily terminated by centrifuging or filtering the reaction mixture, preferably by filtration through a cartridge filter having 1.2 micron pores. However, it is within the scope of this invention to hold the reaction time constant but vary another condition, e.g., if a bulk lot needed little activation the reaction could be conducted at a lower temperature than with a lot needing more vigorous treatment. Activation control by temperature offers an additional advantage in that at lower temperatures, i.e., 0° C. to about 10° C., the production of factor VIIa is favored in comparison to thrombin and factors IXa and Xa. Finally, more than one condition may be varied, but this generally is not preferred.

The activation period will depend upon the extent of activation desired compared to that which has already occured spontaneously in the starting plasma as determined by screening the starting material. The preferred degree of activation, expressed in NAPT time is about from 70 to 100 seconds, preferably 75-95 seconds. The preferred degree of activation may also be expressed as a factor VIII correctional time of about from 70-90 seconds and preferably about 70-80 seconds. The factor VIII correctional time is not preferred for monitoring activation state because the change in clotting time during activation is not as large as that usually encountered in the NAPT time. It is within the scope of this invention to use the NAPT time to the exclusion of the factor VIII correctional time assay as well as the thrombin generation time or FEIBA tests disclosed by Pepper et al., op cit. The clotting times reported herein, unless otherwise stated, are for samples immediately after activation. Further concentration of the activated PCC will reduce the NAPT and factor VIII correctional times, e.g. generally doubling the concentration of clotting factors will approximately halve the NAPT time. Further, a different degree of activation as represented by different predetermined NAPT and factor VIII correctional times may be selected depending upon the clinical uses to which the final product is to be put. Also, the degree of activation may be determined by other assays, e.g., one or more of the activated clotting factor tests described below. The actual elapsed time per se is generally not material, but has been found to range about from 5 to 45 minutes, routinely 15 minutes.

The preferred method for ascertaining the magnitude of time needed for activation for each individual bulk lot of starting material comprises first determining the activation period using aliquots withdrawn from the bulk lot before activation, and then monitoring the lot during activation as well. The first portion of this preferred method comprises removing a plurality of samples from the bulk lot before activation, activating each sample and then stopping the activation at different times. Each aliquot is subsequently assayed for its NAPT and factor VIII correctional times, a plot of the results is made and the period which must elapse for the attainment of the desired NAPT, and optionally factor VIII correctional times, is determined. Also, it is preferred that thrombin be determined as well. The bulk lot is then activated with this period in mind under the same conditions as were used with the aliquot samples. Aliquots of the lot during activation are also taken to confirm its progress.

In more detail, the first portion of the preferred embodiment comprises removing duplicate 110 ml aliquots of sample, mixing about 60 mg of silica with each aliquot at a temperature of 15° C.-20° C., allowing the activation to proceed for 5 minutes and multiples thereof up to 60 minutes, filtering the aliquots to separate the silica, recording the time of activation for each aliquot, and determining the average NAPT and factor VIII correctional times for each aliquot. The activation period required to attain NAPT and factor VIII correctional times, respectively, of about from 70-100 seconds and about from 70-90 seconds is then determined by interpolation. This entire procedure will ordinarily require less than 1.5 hours. During this time the bulk lot from which the samples were withdrawn cam be simply held at 15°-20° C. without any significant changes in the levels of activated factors.

The second portion of the preferred method for determining the proper activation time has the advantage that the effect of the activation procedure on the bulk lot itself is monitored, yielding a more direct result than following the activation of aliquots that are intended to be representative. This portion of the method comprises commencing activation of the screened starting material, withdrawing 10 ml samples from the reaction mixture at 5 minute intervals and assaying each for factor VIII correctional and NAPT times and, optionally, thrombin. When the predetermined factor VIII correctional or NAPT time is projected to be reached within a next 5 minute interval, the activation procedure is stopped by filtrative removal of the silica. It is desirable to extrapolate the assay results because the assays measure the state of activation at the time the sample is taken, and not at the time the results are read. The projection is conventionally based upon a plot of the factor VIII correctional and NAPT times observed earlier during the activation procedure. Any risk that the activation will overshoot the target parameters during the assays is small if the assays are expeditiously conducted.

Following the completion of controlled activation the clotting factors may be further purified to any desired degree, although it is not necessary to do so. It is preferred that the activated PCC be purified and concentrated by PEG precipitation as disclosed in U.S. Pat. No. 3,560,475 and discussed above. Other protein isolation techniques may be used, e.g., adsorption on ion exchange resins, gel chromatography or precipitation by such well known agents as alkanols or Pluronic polymers.

The purified product is dissolved in a volume of aqueous solution equal to about 2% of the fraction IV-1 paste solution. This aqueous solution preferably contains 1 volume of 0.1M sodium citrate, 4 volumes of 0.9% NaCl and from 1 to 2 units of heparin/ml. The pH is adjusted to a physiologically tolerable level, for example 7.0, clarified and sterile filtered by conventional techniques, dispensed into vials and lyophilized. The product is generally reconstituted into sterile water to yield the same concentration as before lyophilization. The reconstituted product will contain from about 0.5 to 1.5 units of heparin/ml, preferably greater than about 1.1 units/ml.

Heparin should be added at the final dissolution of the activated PCC before lyophilization, although it may be added at any point after activation. It is preferable that the heparin be added just prior to lyophilization. Antithrombin III may also be added at this point, although since the product will ordinarily contain about 0.1 International unit of antithrombin/ml it may be unnecessary to add more antithrombin III. If necessary, sufficient antithrombin III and heparin are added to reduce any extraneous thrombin activity in the reconstituted activated PCC to a level lower than about 0.003 units of thrombin/ml.

Clotting Factor Assays

The analytical methods for determining factors XI, XII, II, VII, IX, X, Xa, IX precursor, VIIa and thrombin are generally conventional. All of the assays have certain features in common, unless otherwise specified. First, each assay will include making duplicate serial dilutions of test sample and a standard having an assigned potency of 1 unit/ml. The concentration in units/ml of the test sample may then be calculated by averaging the duplicates, plotting the results obtained with the standards against their respective percent concentrations as established by their previous serial dilution, reading the percent concentrations in the diluted test samples from the plot, correcting the test sample concentrations for the serial dilutions which were made; averaging the test sample percent concentrations and dividing the average by 100 to arrive at the units/ml of the assayed factor.

Second, unless otherwise indicated all assays are conducted at 37° C. and all reagents are prewarmed to that temperature.

Third, assays for total clotting factors use either lyophilized normal human plasma or frozen normal human plasma as standards. The lyophilized normal human plasma is standardized against three separate freshly drawn pools of normal human plasma. Each pool is prepared by collecting venous blood from 10 fasting, normal donors who are not taking oral contraceptives, anti-inflammatory drugs or arthritis medication. The donors must also have a prothrombin time of 11-15 seconds, an APTT of 30-45 seconds and a fibrinogen level of 200-400 mg/dl. The blood is collected into 3.8% sodium citrate at a ratio of 9 volumes of blood to 1 of anticoagulant, mixed, centrifuged at 1000 RCF for 15 minutes, after which equal volumes of each plasma supernatant are pooled. The plasma is assayed within one hour. The average potency of the three pools for each total factor assayed below is arbitrarily set at 1 unit/ml.

The frozen normal human plasma is prepared in identical fashion to any one of the three freshly drawn pools described above, except that the pool is distributed in 1 ml volumes into plastic vials and frozen at −70° C. The frozen pools are used within 60 days. Each frozen pool is considered to contain 1 unit of each total factor/ml. Hereinafter, plasma which contains standard unitage as established by either of the two foregoing techniques will be referred to as reference or standard plasma.

Fourth, the factor deficient plasma used in some assays are plasma obtained from donors that are congenitally deficient in the particular factor, i.e., who have a factor potency of less than about 5% of that present in normal pooled plasma.

Fifth, the F-IX assays detect total and precursor F-IX. The assay for total F-IX measures the sum of activated and unactivated F-IX activity, while the F-IX precursor assay substantially excludes the activated material. Therefore, F-IXa may be estimated by subtracting the precursor activity from the total F-IX. It should be noted that the remaining analytical methods;

i.e., for factors II, VII, X, XI and XII, all measures the sum of active and proenzyme factor. However, in the interests of brevity the designation "total" will not be applied to these assays. On the other hand, and in contrast to the F-IX methods, the thrombin, VIIa and Xa methods disclosed below directly assay the active factors.

Thrombin is determined by the following technique. A bovine thrombin standard, which has been standardized against the NIH Thrombin Standard, lot B-3, is diluted in normal saline to 0.001, 0.002, 0.003, 0.005 and 0.010 u/ml. 2.0 ml of this diluted standard is added to 0.5 ml of fibrinogen substrate. The mixture is incubated at 28° C. The reaction tubes are checked every 2 minutes. First fibrin strand appearance is taken as the end point. The test sample is assayed identically, but with no dilution. Thus, 2.0 ml of the reconstituted test sample is added to 0.5 ml of the fibrinogen substrate and end point formation is observed at 2 minute intervals. The clotting times of the test sample are compared with the clotting times of the thrombin standard. The calculations are conducted as generally described above.

Factor Xa is determined by a modification of the method of Yin et al., "J. Lab. Clin. Med." 81:298(1973). All reagents, including the reference standard, are commercially available from the Sigma Chemical Company. Test samples are serially diluted in duplicate into the buffer employed by Yin et al. at dilutions of 1:8, 1:16 and 1:32, or higher (expressed in parts of sample to parts of buffer) until the clotting time of that dilution is longer than the clotting time of the factor Xa standard at a concentration of 0.01 units/ml.

Standard factor Xa is initially diluted 1:4 into the same buffer, followed by serial dilutions in duplicate to 1:64. A 1:4 dilution of standard F-Xa is taken as 1 unit F-Xa/ml. Standard F-Xa is defined as that which will produce an average clotting time of 14 seconds at 1:2 dilution in the assay described herein. 0.1 ml of each final dilution is pipetted into a fibrometer cup, followed by 0.1 ml of 0.025M $CaCl_2$ and 0.2 ml of a bovine plasma-rabbit cephalin solution to initiate clotting. The clotting time for each tube is determined and the F-Xa activity calculated as described above.

F-Xa may also be determined by a chromogenic assay as an alternative to the clotting method described in the preceding paragraph. Unless otherwise stated by designation of the assay results as "chromogenic" it will be assumed that the F-Xa was determined by the clotting method. The chromogenic assay is essentially disclosed by Kosow in "Thrombosis Research" 1:565-573 (1976). It employs a synthetic substrate which is specifically hydrolyzed by F-Xa to yield a chromogen detectable by its adsorption of light at 405 nm. The substrate, S-2222, is commercially available from Ortho Diagnostics, Inc. Standard F-Xa is available from the Sigma Chemical Co., but is diluted 1:4 into 0.05M Tris buffer at pH 8.3 containing 1.33% NaCl by weight before use. A 1:4 dilution of a standard containing 0.5 unit F-Xa/ml should exhibit an average optical density at 405 nm of 0.260 in the assay. In the practice of the assay, samples and diluted standard are serially diluted into the Tris buffer. 0.4 ml of each dilution is pipetted into a glass test tube, followed by 0.075 ml of a solution containing 0.5M $CaCl_2$ and 0.1M NaCl and, after 1 minute, 0.5 ml of an S-2222 solution in 0.05M Tris buffer at pH 8.3 containing 0.9% NaCl by weight. 0.1 ml of 50% acetic acid is added after 3 minutes to stop the reaction and the absorbance is read against a buffer blank at 405 nm. The calculations are conducted as generally described above.

Factor X is determined by a modification of the Bachmann et al. method described in "Thromb. et Diath." 2:24(1958) except that factor X deficient plasma is used in place of Seitz filtered ox plasma, a fibrometer is used for end point detection and the diluting fluid is veronal buffer containing sodium chloride and sodium citrate as described by Proctor et al., "Am. J. Clin. Path." 36(3):214(1961). Russell's viper venom and cephalin were obtained from Burroughs Wellcome & Co. and the Hyland Division of Travenol Laboratories, Inc., respectively. The calculations are made as generally described above.

Prothrombin (factor II) is assayed by the following technique. 0.1 ml of factor II deficient plasma prepared by the method of Pechet in Tocantins, Ed., *Blood Coagulation, Hemorrhage and Thrombosis*, volume 1, pp 144-148 (1964) is distributed into each of eight test tubes. A 100% reference plasma is prepared by diluting reference plasma 1:10 into 1.72% imidazole weight-/volume buffer at pH 7.3. This reference plasma is then further diluted 1:5, 1:10, 1:20 and 1:40 into the same buffer. Duplicate 0.1 ml aliquots of each dilution are pipetted into the test tubes containing factor II deficient substrate. Immediately after pipetting the reference plasma into each duplicate set of test tubes, 0.2 ml of rabbit brain thromboplastin lyophilized with $CaCl_2$ is added to each test tube by means of a plastic-tipped pipette. After mixing for 15 seconds each tube is tilted back and forth once per second over a light source and the time that elapses before final gel formation is recorded. The foregoing procedure is repeated with the test sample, except that a 1:100 dilution into imidazole buffer is made before the 1:5, 1:10, 1:20 and 1:40 dilutions. The data is handled in the same fashion as discussed above.

F-IX is determined by the following procedure, essentially that of Proctor et al., op cit. A minimum 1:20 predilution of the activated PCC test sample is prepared in normal saline. Reference plasma is not prediluted. Then duplicate 1:5, 1:10, 1:20 and 1:40 dilutions in barbital buffered saline of test sample and reference plasma are pipetted into test tubes already containing 0.1 ml of partial thromboplastin-kaolin described in the Proctor et al. procedure and 0.1 ml of F-IX congenitally deficient plasma having less than 5% of normal F-IX activity. After 3 minutes, 0.1 ml of 0.03M $CaCl_2$ is mixed with the contents of each test tube, incubated for 30 seconds and then each test tube is tilted at less than once per second in front of a light source until final gel formation. The time from $CaCl_2$ addition to gel formation is recorded and the data treated as generally described above.

F-IX precursor is assayed exactly as set forth above for total F-IX except that the initial minimum 1:20 dilutions of test sample are made up in the F-IX deficient substrate rather than normal saline.

Factor VII is determined according to Esnouf et al. in Bang et al., Ed., *"Thrombosis and Bleeding Disorders, Theory and Methods,"* pp 197-198, (1971) except that the clotting point was determined with a Clotek ® device and the diluting fluid was that described by Proctor et al. op cit.

Factor VIIa is assayed by first adsorbing the sample with a benzamidine-Sepharose affinity matrix. The benzamidine-Sepharose matrix is a well known affinity gel disclosed, for example, by Schmer, "Z. Physiol. Chem."

353: 810-814 (1972). The non-adsorbed fraction is removed from the matrix by washing with 0.1M NaHCO$_3$, ph 7.8. Then, the same buffer containing 0.5M NaCl and 0.3M benzamidine HCl is used to remove the fraction containing VIIa. Assay of the latter fraction for VIIa is acomplished with the same assay and reference which are used for F-VII.

The assay for factor XI is described by Rappaport et al. in "J. Lab. Clin. Med." 57:771(1961), except that the CaCl$_2$ solution is 0.03M, a cephalin-kaolin mixture commercially available from the Hyland Division of Travenol Laboratories, Inc. was employed, and the clotting point was determined with a Clotek ® device.

Factor XII is determined in essentially the same way as factor XI. However, here a factor XII deficient plasma is used and the assay is only conducted in contact with plastic ware.

The novel activated products of this invention are characterized by the amounts or activities of individual clotting factors, overall procoagulant activity as reflected in the NAPT and F-VIII correctional times, substantial freedom from thrombin activity and substances which induce an immune response to F-VIII in treated patients, greater than 1 unit of heparin/ml and the presence of about 0.1 to 3 units antithrombin III/ml in the final product. Combinations of any or all of the foregoing features also characterize the products of this invention.

The typical, preferred and most preferred ranges of clotting factor activities in the activated PCC of this invention fall within the limits set forth in Table 1 below. In addition to the components set forth in Table 1 the products may optionally also contain about from 3 to 65 units of F-XI and 1 to 30 units of F-XII/ml.

TABLE 1
ACTIVATED PCC CLOTTING FACTOR LEVELS

| Factor | Range in units/ml | | |
| --- | --- | --- | --- |
|  | Typical | Preferred | Most Preferred |
| II | 1-10 | 3.6-8.9 | 3.6-5.9 |
| VII | 37-190 | 37-122 | 39-88 |
| VIIa | 8-80 | 25-78 | 25-60 |
| IX | 15-112 | 20-81 | 50-80 |
| IX Precursor | 0-30 | 5-20 | 5-12 |
| X | 1-30 | 1-25 | 1-13 |
| Xa | 1-20 | 1-10 | 4-10 |
| Xa (Chromogenic) | 1-10 | 1-8 | 1-5 |
| Thrombin | 0.003 | 0.002 | 0.001 |

Obviously the ranges for each of these factors expressed in units/ml will depend upon the reconstitution volume of the activated PCC, which may be varied depending upon the intended use for the product. Thus the above ranges in units/ml may also be considered the relative proportionate units on a dry weight basis, the actual concentration in units per milliliter depending upon the reconstitution volume of the activated PCC. The ranges given above are for activated PCC which is diluted or reconstituted for direct administration to a patient.

A preferred composition of this invention comprises, in units/ml, about from 20 to 112 units of F-IX and from 0 to about 30 units of F-IX precursor.

Another preferred compositions of this invention comprises, in units/ml, about from 37 to 190 units of F-VII and about from 25 to 80 units of F-VIIa.

A further preferred composition of this invention comprises, in units/ml, about from 1 to 13 units of F-X and about from 4 to 10 units of F-Xa.

This invention also includes a product comprising factors VIIa, IXa and Xa and having a F-VIII correctional activity of about from 1 to 35 units/ml and a NAPT time of about from 27 to 70 seconds/ml. The preferred composition exhibits a F-VIII correctional activity of about from 7 to 30 units/ml.

The activated PCC of this invention may be administered to patients in the same fashion as PCC has heretofore been administered. Conventionally, the contents of vials containing lyophilized, activated PCC are reconstituted in sterile water and infused at a therapeutically effective dosage, generally ranging about from 8 to 160 F-VIII correctional units/kg and preferably about from 10 to 80 F-VIII correctional units/kg. Optimal results are obtained with dosages of greater than about 25 F-VIII correctional units/kg, preferably 50 units/kg. If required, the dosage may be repeated at 6 to 8 hour intervals. Total dosages of activated PCC on rare occasions have ranged up to about 2000 F-VIII correctional units/kg; satisfactory therapy is usually seen at total dosages of about from 8 to 300 F-VIII correctional units/kg, preferably about from 10 to 100 F-VIII correctional units/kg. Since total dosage refers to the quantity of F-VIII correctional activity administered during a bleeding episode rather than the amount administered during any one infusion, it can be seen that one infusion is frequently effective in achieving clinically satisfactory results.

One embodiment of therapeutic treatment is the administration of a therapeutically effective dose of an aqueous composition comprising about from 20 to 112 units of F-IX/ml and from 0 to about 30 units of F-IX precursor/ml to a patient exhibiting a clotting factor inhibitor.

Another embodiment of the therapeutic method of this invention contemplates the administration of a therapeutically effective dose of an aqueous composition comprising about from 37 to 110 units of F-VII/ml and about from 8 to 80 units of F-VIIa/ml to a patient exhibiting a clotting factor inhibitor.

An additional embodiment of this invention is the administration of a therapeutically effective dose of an aqueous composition comprising about from 1 to 50 units of F-X/ml and about from 4 to 10 units of F-Xa/ml to a patient exhibiting a clotting factor inhibitor.

This invention will be more fully understood by reference to the following examples.

EXAMPLE I

Manufacture of Activated Prothombin Complex

This example discloses a typical manufacturing run for the controlled preparation of an activated PCC.

80 kgs of Cohn fraction IV-1 paste are suspended in 720 liters of saline and the pH adjusted to 7.2 with 1N sodium hydroxide. A resultant heavy sediment is allowed to settle, after which a clear supernatant is obtained by centrifugation. The NAPT and factor VIII correctional times were determined to be 240 and 98 seconds, respectively. As these times fall within the criteria of greater than 200 and 89 seconds, respectively, the lot was selected for activation. 3.6 kgs of calcium phosphate are added to the clarified supernatant. After 15 minutes mixing the suspension is centrifuged to recover the calcium phosphate-absorbed coagulation factors. The factors are separated from the calcium phosphate by vigorous mixing for 5 minutes with a volume of 0.1M sodium citrate equal to 4% of the dissolved IV-1 paste volume. The suspension is centrifuged and the supernatant recovered.

The coagulation factors in the supernatant are then activated by adding 20.9 gm of silica to the supernatant and continuously mixing. 10 ml samples are withdrawn at 5 minute intervals and the degree of activation determined by the NAPT and factor VIII correctional times, and thrombin assays described above.

The silica induced activation is terminated by filtration of the reaction mixture through a 1.2 micron cartridge when the NAPT and factor VIII correctional times reached 90 and within 70-90 seconds, respectively. The thrombin activity at this point was below 0.003 units/ml.

The activated PCC is next further purified by the PEG precipitation steps disclosed in U.S. Pat. No. 3,560,475. The filtrate from the silica removal step is brought to 5% weight/volume PEG by the addition of 1.4 kg PEG having an average molecular weight of 4000 (PEG-4000). The suspension is centrifuged after mixing for approximately 15 minutes, its pH adjusted to 5.2 and the supernatant brought to 20% PEG-4000 by the further addition of 4.1 kgs of PET. The suspension is centrifuged after mixing for approximately 15 minutes, and the precipitate collected. The precipitate is dissolved in 0.02M sodium citrate containing 0.72% NaCl and 1.5 units heparin/ml, the pH adjusted to 7.0, clarified, sterile filtered, filled into 30 ml vials and lyophilized. The factor VIII correctional and NAPT activities and the levels of clotting factors in this preparation reconstituted in water are set forth in Table 2.

TABLE 2

| Factor or Activity | Activity (in units/ml unless otherwise noted) |
|---|---|
| II | 7.8 |
| VII | 47.6 |
| VIIa | 58.8 |
| IX | 39.2 |
| IX Precursor | 11.5 |
| X | 9.3 |
| Xa | 1.6 |
| Thrombin | 0.002 |
| Factor VIII correctional | 21.2 |
| NAPT time (1:100 dilution) | 45.6 (seconds) |

EXAMPLE II

The process of Example I was substantially repeated on 10 more lots of PCC. The results are shown in Table 3 below.

EXAMPLE III

The products of this invention were distributed to 13 investigators for an evaluation of clinical efficacy. 33 patients in all were treated for a total of 74 bleeding episodes. All of the patients but one exhibited various levels of factor VIII antibody; the patient not having factor VIII antibody is additionally reported in Example IV. The bleeding episodes among these patients predominantly involved the joints (59.5%), while soft tissue (14.8%) and combination joint and soft tissue bleeds (5.4%) accounted for the bulk of the remainder. Of the remaining 15 patients ten (13.5%) were surgically oriented, three exhibited hematuria, one hematemesis and one intracranial bleed.

The population of total administered doses, some over multiple infusions, ranged from 9 to 1,861 factor VIII correctional units/kg. The distribution of doses is further discussed below in connection with patient prothrombin time (PT) and activated partial thromboplastin time (PTT), Tables 4 and 5. Each dosage was administered by infusion in sterile water for injection. In most cases a single infusion of about 30 ml was sufficient to achieve a moderate or excellent clinical response, although more than one dose was administered in a number of the bleeding episodes.

Clinical performance of the activated PCC was subjectively evaluated by each investigator within eight hours after the infusion. While evaluations were made on the overall clinical response the investigators focused on hemostasis, pain relief and improvements in joint motion. In general, an "excellent" overall clinical response meant abrupt pain relief and unequivocal decrease in joint or bleed site size, usually within eight hours after a single infusion. A "moderate" overall clinical response was defined as definite but slightly delayed pain and bleed site relief which, in some cases, required more than one infusion. A "fair" overall clinical response meant an unclear, but probable beneficial effect requiring still more infusions. An overall clinical response designated as "none" meant no effect relative to pain, range of joint motion, or degree of swelling of the bleeding site.

The overall clinical response resulting from the treatment with the products in the 74 bleeding episodes is summarized in Table 3. For convenience the factor VIII correctional activity dosage was divided into two groups, those above and below 50 units/kg.

TABLE 3

RESULTS OF TESTS PERFORMED ON FINAL CONTAINERS OF 10 LOTS OF ACTIVATED PCC
(All potency values expressed as units/ml except as otherwise noted)

| Lot Number | F-II | F-VII | F-VIIa | F-VIII Correction | F-IX | F-IX Precursor | F-X | F-Xa | Thrombin | APT (Seconds) |
|---|---|---|---|---|---|---|---|---|---|---|
| 0650D010 | 7.1 | 63.4 | 77.8 | 25.8 (11.6$^a$) | 66.7 | 8.6 | 11.1 | 7.2 | 0.002 | 27.3 |
| 0650D012 | 3.6 | 39.0 | 25.4 | 7.7$^a$ | 23.2 | 6.1 | 10.4 | 3.5 | 0.001 | 41.1 |
| 0650D013 | 7.1 | 47.0 | 58.8 | 9.0$^a$ | 40.3 | 6.3 | 12.5 | 5.2 | 0.001 | 39.7 |
| 0650D014 | 7.2 | 65.9 | 35.2 | 9.9$^a$ | 55.2 | 10.3 | 10.2 | 4.1 | 0.001 | 39.7 |
| 0650D018 | 5.6 | 68.3 | 32.5 | 8.8$^a$ | 54.8 | 10.3 | 14.7 | 4.8 | 0.001 | 37.3 |
| 0650D021 | 5.3 | 65.5 | 40.1 | 14.5 | 34.7 | 8.3 | 11.0 | 2.2 | 0.001 | 54.4 |
| 0650D024 | 8.9 | 63.5 | 36.0 | 27.6 | 112.3 | 36.3 | 24.2 | 7.6 | 0.001 | 38.9 |
| 0650E021 | 3.8 | 71.9 | 25.8 | 16.7 | 70.1 | 5.0 | 10.4 | 6.8 | 0.001 | 34.1 |
| 0650D028 | 5.2 | 77.0 | N.D.$^b$ | 14.9 | 50.9 | 9.5 | 11.7 | 4.3 | 0.001 | 35.5 |
| 0650E003 | 7.1 | 88.0 | N.D. | 20.0 | 54.1 | N.D. | 9.1 | 2.2 | 0.001 | 39.5 |

$^a$Kaolin was substituted for soluble ellagic acid in the assay.
$^b$N.D. = not done.

TABLE 3

Overall Clinical Response

| Rating | Total | % Total | Patients Dosed With greater than 50 U/kg (Total) | Patients Dosed With less than 50 U/kg (Total) |
|---|---|---|---|---|
| Excellent | 43 | 58.1 | 33/50 (66.0%) | 10/24 (41.6%) |
| Moderate | 22 | 29.7 | 10/50 (20.0%) | 12/24 (50.0%) |
| Fair | 6 | 8.1 | 5/50 (10.0%) | 1/24 (4.2%) |
| None | 3 | 4.1 | 2/50 (4.0%) | 1/24 (4.2%) |
| TOTAL | 74 | 100.0 | 50/74 (67.6%) | 24/74 (32.4%) |

Of the total bleeds, 43 or 58.1% were categorized by the investigators as exhibiting an excellent clinical response. Combining excellent clinical responses with moderate responses resulted in favorable results for 65 (87.8%) of the total bleeding episodes. Nine bleeding episodes (12.2%) were categorized by the investigators as fair or no clinical response, the latter accounting for three of the nine bleeding episodes.

Table 3 further shows that of the 50 bleeding episodes receiving doses greater than 50 units of factor VIII correctional activity/kg, 33 or 66% exhibited an excellent clinical response while only 10 (or 41.6%) of the 24 episodes dosed with less than 50 units had an excellent response. Thus it is concluded that a dosage of greater than 50 units of factor VIII correctional activity/kg is preferred for the best therapeutic treatment of bleeding episodes.

Of the three bleeding episodes where no clinical response occurred, one patient was treated initially with relatively low doses of product (10 units/kg and 22 hours later with 21 units/kg). Not until after the patient received two additional doses of 42 units/kg (each approximately 22 hours apart) in conjunction with the application of a plaster splint did some gradual improvement take place.

The second patient exhibited slight improvement after the first of three infusions of 31.8 units/kg. However, the subsequent doses provded to be of no benefit and the patient was switched to factor VIII therapy. After three doses of factor VIII (3,500 units) slow improvement in the bleed occurred.

The third patient received only a small, single infusion of product (39.1 units/kg).

Since it is extremely important in the control of bleeding episodes to achieve rapid remission of symptoms the data were arranged to demonstrate the effect of single doses of the invention product. Table 4 summarizes the results.

TABLE 4

Overall Clinical Response After A Single Dose

| Rating | Total | % Total | Patients' Initial Dose >50 U/kg | Patients' Initial Dose <50 U/kg |
|---|---|---|---|---|
| Excellent | 40 | 66.6 | 28 (87.5%) | 12 (42.8%) |
| Moderate | 18 | 30.0 | 3 (9.4%) | 15 (53.6%) |
| Fair | 1 | 1.7 | 1 (3.1%) | 0 (0%) |
| None | 1 | 1.7 | 0 (0%) | 1 (3.6%) |
| TOTAL | 60 | 100.0 | 32/60 (53.3%) | 28/60 (46.7%) |

It can be seen that considerably better results are achieved with doses of 50 U/kg or greater.

The correlation among activated PCC dose, post-infusion PTT and PT assays, and clinical response was investigated by determining the minimal and maximal PT and PTT decrease from pre-infusion to post-infusion, a span varying between 15 minutes and 2 hours. The results are set forth in Tables 5 and 6 as differences from control times, i.e., delta differences. The units are factor VIII correctional units.

TABLE 5

Change in PTT after Initial Infusion

| Dose Range (U/kg) | Δ PTT Range (Sec.) | Total | Excellent | Moderate | Fair | None |
|---|---|---|---|---|---|---|
| 7.9–39.1 | 1.1–14.5 | 21 | 9 | 11 | 0 | 1 |
| 31.5–50.1 | 16.0–61.5 | 4 | 2 | 2 | 0 | 0 |
| 52.0–100.0 | 16.9–46.3 | 20 | 15 | 3 | 1 | 1 |
| 57.5–103.0 | 1.6–14.5 | 6 | 5 | 1 | 0 | 0 |

TABLE 6

Change in PT after Initial Infusion

| Dose Range (U/Kg) | Δ PT Range (Sec.) | Total | Excellent | Moderate | Fair | None |
|---|---|---|---|---|---|---|
| 5.3–39.1 | 1.3–1.9 | 5 | 2 | 2 | 0 | 1 |
| 7.9–50.0 | 2.4–5.2 | 21 | 9 | 12 | 0 | 0 |
| 52.0–103.0 | 2.0–7.0 | 21 | 17 | 3 | 0 | 1 |
| 55.0–100.0 | 0.5–1.7 | 6 | 5 | 1 | 0 | 0 |

In conclusion, 74 bleeding episodes were treated with the product of this invention in 33 patients that exhibited clotting factor deficiencies, primarily factor VIII inhibitor. 71 of these 74 episodes resulted in a beneficial clinical response. 59 of the 71 required but one infusion to produce a beneficial clinical response, which occurred in 55 out of 59 cases within eight hours of the infusion. Six required two infusions and six required three or more infusions to produce a beneficial clinical response.

The greatest reduction in both the PTT and PT values occurred with doses above 50 units of factor VIII correctional activity/kg and were in conjunction with greater beneficial clinical results.

EXAMPLE IV

One of the patients in the clinical study reported in Example III had a history of factor XI deficiency. In addition, factor XI inhibitor was observed. This patient had a spontaneous left thigh bleed for which he initially received one liter/day of fresh frozen plasma on hospital days one through seven. The product of this invention was administered on days 10 through 13. The overall clinical response after four infusions totalling 177 factor VIII correctional units/kg was rated by the investigator as moderate. The investigator commented that "most likely the patient would have lost the use of his leg due to the bleed without the availability of the product."

I claim:

1. A method for treating a patient having an inhibitor of a blood clotting factor, which comprises administering to the patient a therapeutically effective dose of an aqueous composition comprising about from 20 to 112 units of F-IX/ml and from 0 to about 30 units of F-IX precursor/ml.

2. A method for treating a patient having an inhibitor of a blood clotting factor, which comprises administering to the patient a therapeutically effective dose of an aqueous composition comprising about from 1 to 50 units of F-X/ml and about from 4 to 10 units of F-Xa/ml.

3. The method of claims 1 or 2 wherein the therapeutically effective dose is greater than about 25 factor VIII correctional units/kg of patient weight.

4. The method of claims 1 or 2 wherein the aqueous composition additionally comprises greater than 1.1 units of heparin/ml.

5. The method of claims 1 or 2 wherein the aqueous composition additionally comprises antithrombin III.

6. The method of claims 1 or 2 wherein the aqueous composition is sufficiently free of factor VIII antigen to not provoke an immune response in the patient to factor VIII.

7. A composition for the treatment of clotting factor deficiencies and inhibitors which comprises, in relative proportionate units, prothrombin, about from 1–10; thrombin, less than about 0.003, factor VII, about from 37–190; factor VIIa about from 8–80; factor IX, about from 15–112; factor IX precursor, 9 to about 30; factor X, about from 1–30; and factor Xa about from 1–10.

8. A composition for the treatment of clotting factor inhibitors which comprises, in relative proportionate units, prothrombin, about from 3.6–8.9; thrombin, less than about 0.002, factor VII, about from 37–122; factor VIIa about from 25–78; factor IX, about from 20–81; factor IX precursor, 5 to about 20; factor X about from 1–25; and factor Xa about from 2–10.

9. A composition for the treatment of clotting factor inhibitors which comprises, in relative proportionate units, prothrombin, about from 3.6–5.9; thrombin, less than about 0.001, factor VII, about from 39–88; factor VIIa about from 25–60; factor IX, about from 50–80; factor IX precursor, 5 to about 12; factor X about from 1–13; and factor Xa about from 4–10.

10. A composition for treating clotting factor inhibitors which comprises about from 20–112 proportionate units of factor IX and above 0 to about 30 units of factor IX precursor.

11. An aqueous composition for treating clotting factor inhibitors which comprises about from 1 to 13 units of F-X/ml and about from 4 to 10 units of F-Xa/ml.

12. The compositions of claims 6, 7, 8 or 9 additionally comprising greater than 1.1 proportionate units of heparin.

13. The composition of claim 12 additionally comprising antithrombin III.

14. The composition of claims 7, 8, 9 or 10 which is sufficiently free of factor VIII antigen to not provoke an immune response to factor VIII in humans.

15. The composition of claims 7, 8 or 9 dissolved in aqueous solution.

16. The composition of claim 10 dissolved in an aqueous solution to a concentration of about from 20–112 units of factor IX/ml and about 0 to about 30 units of factor IX precursor/ml.

17. The composition of claim 10 further including about from 8 to 80 proportionate units of factor VIIa.

18. The composition of claim 10 containing about from 25 to 78 proportionate units of factor VIIa.

* * * * *

UNITED STATES PATENT AND TRADEMARK OFFICE
CERTIFICATE OF CORRECTION

PATENT NO. : 4,459,288  Page 1 of 2
DATED : July 10, 1984
INVENTOR(S) : William R. Thomas It is certified that error appears in the above-identified patent and that said Letters Patent are hereby corrected as shown below:

Column 2, line 61, change "cotting" to --clotting--

Column 3, line 57, underline in vivo

Column 6, line 16, underline 36

Column 8, line 35, underline op cit

Column 8, line 48, underline per se

Column 9, line 15, change "cam" to --can--

Column 11, line 1, change "measures" to --measure--

UNITED STATES PATENT AND TRADEMARK OFFICE
CERTIFICATE OF CORRECTION

PATENT NO. : 4,459,288   Page 2 of 2
DATED : July 10, 1984
INVENTOR(S) : William R. Thomas It is certified that error appears in the above—identified patent and that said Letters Patent are hereby corrected as shown below:

Column 11, line 24, underline 81

Column 12, line 39, underline op cit

Table 3, change "APT" to --NAPT--; FVIIa value for Lot Number 0650D014 should read --39.2--; F-VIII Correction for Lot Number 0650D028 should read --0.9--; FVIII Correction for Lot Number 0650E003 should read --1.0$^a$--

Column 20, line 6, after 30 please insert --proportionate--

Signed and Sealed this

Fifth Day of February 1985

[SEAL]

Attest:

DONALD J. QUIGG

Attesting Officer    Acting Commissioner of Patents and Trademarks